(12) United States Patent
Louis

(10) Patent No.: US 9,388,128 B2
(45) Date of Patent: *Jul. 12, 2016

(54) PROCESS FOR THE MANUFACTURE OF DIHALODIPHENYLSULFONES STARTING FROM ORGANIC ACIDS

(75) Inventor: Chantal Louis, Alpharetta, GA (US)

(73) Assignee: SOLVAY SPECIALITY POLYMERS USA, LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/111,904

(22) PCT Filed: Apr. 12, 2012

(86) PCT No.: PCT/EP2012/056611
§ 371 (c)(1),
(2), (4) Date: Oct. 15, 2013

(87) PCT Pub. No.: WO2012/143279
PCT Pub. Date: Oct. 26, 2012

(65) Prior Publication Data
US 2014/0228597 A1    Aug. 14, 2014

Related U.S. Application Data

(60) Provisional application No. 61/476,413, filed on Apr. 18, 2011.

(51) Int. Cl.
C07C 315/02     (2006.01)
C07C 315/00     (2006.01)

(52) U.S. Cl.
CPC ............. C07C 315/02 (2013.01); C07C 315/00 (2013.01)

(58) Field of Classification Search
USPC .......................................... 568/28, 34, 35, 36
See application file for complete search history.

(56) References Cited

U.S. PATENT DOCUMENTS

| 3,415,887 | A | | 12/1968 | Keogh et al. |
| 3,946,037 | A | † | 3/1976 | Koebner |
| 4,937,387 | A | † | 6/1990 | Steiner |
| 4,983,773 | A | | 1/1991 | Stumpp et al. |
| 6,281,309 | B1 | | 8/2001 | Babcock et al. |
| 2012/0302795 | A1 | † | 11/2012 | Bandodkar |

FOREIGN PATENT DOCUMENTS

| CN | 102304071 A | 1/2012 |
| WO | 2011067649 A2 | 6/2011 |
| WO | WO 2012/143281 A1 | 10/2012 |

OTHER PUBLICATIONS

Gilbert; Industrial and Engineering Chemistry, 1953, vol. 45, No. 9, p. 2065-2072.*
Tyobeka; Journal of the Chemical Society, Chemical Communications, Jan. 1, 1980, p. 114-115.*
Hancock; Journal of Chemical Research (S), 1980, p. 270-271.*
Bourne E.J. et al., "155. Studies of trifluoroacetic acid. Part III. The use of trifluoroacetic anhydride in the synthesis of aromatic ketones and sulphones", J. Chem. Soc., 1951, p. 718-720—DOI:10.1039/JR9510000718.
Tyobeka T.E. et al., "The interaction of hexafluoroacetic anhydride with methane sulfonic acid and with sulphuric acid", Tetrahedron, 1988, vol. 44, n°7, p. 1971-1978 , 1988 Pergamon Press.
Alizadeh A. et al., "Rapid and mild sulfonylation of aromatic compounds with sulfonic acids via mixed anhydrides using Tf2O", Tetrahedron Letters, 2007, vol. 48, p. 6805-6808—Elsevier Ltd.
Gilbert, et al., Sulfonation and Sulfation with Sulfur Trioxide, Industrial and Engineering Chemistry, 1953, vol. 45, No. 9, p. 2065-2072.†

* cited by examiner
† cited by third party

Primary Examiner — Pancham Bakshi
(74) Attorney, Agent, or Firm — Jarrod N. Raphael; Dwight M. Benner, II

(57) ABSTRACT

A process for the preparation of dihalodiphenylsulfones such as 4,4'-dichlorodiphenyl sulfone or 4,4'-bis-(4-chlorophenyl-sulfonyl)biphenyl with high regioselectivity, at low temperature and in the absence of toxic reagents by reacting together at least one acid, sulfur trioxide and at least one halobenzene. The invented process is particularly suited for the manufacture of 4,4'-dichlorodiphenyl sulfone.

23 Claims, No Drawings

PROCESS FOR THE MANUFACTURE OF DIHALODIPHENYLSULFONES STARTING FROM ORGANIC ACIDS

This application is a U.S. national stage entry under 35 U.S.C. §371 of International Application No. PCT/EP2012/056611, filed Apr. 12, 2012, which claims priority to U.S. Application No. 61/476,413 filed on Apr. 18, 2011, and the whole content of these applications is hereby incorporated herein by reference for all purposes.

FIELD OF THE INVENTION

The present invention relates to a new process for the manufacture of dihalodiphenylsulfones such as 4,4'-dichlorodiphenyl sulfone.

BACKGROUND OF THE INVENTION 4,4'-Dichlorodiphenyl sulfone, abbreviated as DCDPS, is an organic sulfone with the formula $(ClC_6H_4)_2SO_2$. It is most commonly used as a key monomer in the manufacture of sulfone polymers.

Other dihalodiphenylsulfones than 4,4'-dichlorodiphenyl sulfone and related derivatives are also of great industrial importance. One can mention inter alia 4,4'-bis-(4-chlorophenylsulfonyl)biphenyl or 4,4'-bis-(4-chlorophenylsulfonyl)terphenyl.

DCDPS can be prepared by various ways. It is generally prepared by a two-step Friedel-Crafts sulfonation and sulfonylation reaction.

DCDPS can be synthesized as described by U.S. Pat. No. 4,983,773 by treating chlorobenzene with sulfuric acid at a temperature of 200-250° C. The reaction can be done in the presence of boric acid or trifluoromethanesulfonic acid, which increases the DCDPS yield by reducing the formation of the 2,4' and 3,4' isomers. The reaction goes to completion in approximately 10 hours and produces a high yield of 4,4'-dichlorodiphenyl sulfone.

Cl-Ph+H$_2$SO$_4$→Cl-Ph-SO$_3$H+H$_2$O

Cl-Ph+Cl-Ph-SO$_3$H→Cl-Ph-SO$_2$-Ph-Cl+H$_2$O

The use of high temperature leads to a decrease in selectivity (80-87% of the 4,4'-isomer) and also requires the use of expensive corrosion resistant material of construction.

The use of lower temperatures has also been described. It gives a higher regioselectivity but requires activated substrates.

U.S. Pat. No. 3,415,887 describes the synthesis of DCDPS starting from sulfur trioxide, diethylsulfate and chlorobenzene. The reaction is exothermic and external cooling must be employed to maintain the temperature to a level not greater than about 15° C. in order to limit the decomposition of intermediate products. The reaction is carried out at lower temperatures and leads to a higher regioselectivity. Dimethylsulfate may also be used in replacement of diethylsulfate. However, the use of diethylsulfate or dimethylsulfate has been firmly discouraged because of their great toxicity which causes significant issues associated with their use and transportation.

Thus, there remains an important need for an alternate route to manufacture dihalodiphenylsulfones and related derivatives with a high yield and high regioselectivity, at low temperature and in the absence of toxic reagents.

THE INVENTION

These needs are met by a process according to the present invention which allows the preparation of a molecule (M) of the formula:

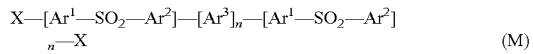

wherein n and m are independently 0, 1, 2, 3 or 4;
wherein X is an halogen selected from chlorine, fluorine, bromine and iodine;
wherein Ar$^1$, Ar$^2$ are equal or different from each other and are aromatic moieties of the formula:

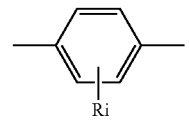

wherein Ar$^3$ is selected from the group consisting of:

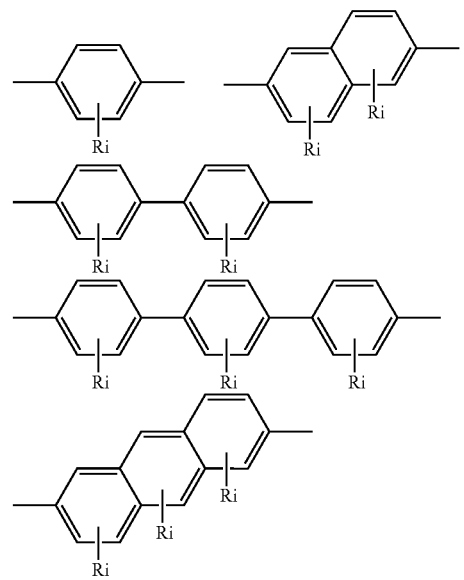

wherein each Ri is independently selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
by reacting together at least one acid, sulfur trioxide and at least one halobenzene.

The process according to the present invention provides a lower cost alternate route to prepare the above mentioned molecules and in particular DCDPS at low temperature (below 200° C.) and high regioselectivity, without the use of expensive corrosion resistant material of construction.

DETAILED DESCRIPTION OF THE INVENTION

The present is directed to a process which allows the preparation of a molecule (M) of the formula:

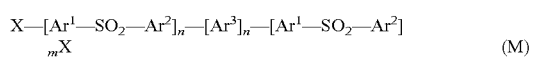

as above described by reacting together at least one acid, sulfur trioxide and at least one halobenzene.

In the molecule (M), n and m are preferably independently 0, 1 or 2, more preferably n and m are 0 or 1. Also, X is preferably selected from F and Cl. In addition, Ri are preferably independently selected from the group consisting of hydrogens and halogens, more preferably all Ri's are hydrogens.

According to the present invention, the above mentioned "molecule (M) may notably be one of the following molecules:

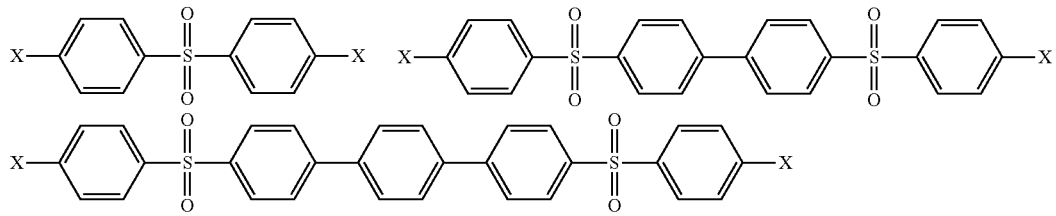

where X may be the same or different and are any halogen atoms chosen from chlorine, fluorine, bromine and iodine. The above structure may also be substituted by groups similar to the Ri described above.

In other words, the molecule (M) may be a dihalodiphenylsulfone such as 4,4'-dichlorodiphenyl sulfone, 4,4'-difluorodiphenyl sulfone, 4,4'-dibromodiphenyl sulfone and 4,4'-diiododiphenyl sulfone or mixed derivatives. Excellent results were obtained for the preparation of 4,4'-dichlorodiphenyl sulfone.

The molecule (M) may also be 4,4'-bis-(4-chlorophenylsulfonyl)biphenyl or 4,4''-bis-(4-chlorophenylsulfonyl)terphenyl.

In the process according to the present invention, the molecule (M) is prepared by reacting together at least one acid, sulfur trioxide and at least one halobenzene.

Each one of the reagents used during the invented process are preferably dry and feature preferably a purity level of at least 95%, more preferably at least 98% and most preferably at least 99%.

The "at least one acid" used in the process according to the present invention may be selected from the group consisting of phosphonic acid, boric acid ($H_3BO_3$), boronic acid (an alkyl or aryl substituted boric acid), sulfonic, carboxylic acids or mixtures thereof. Preferably, it is selected from the group consisting of phosphonic, sulfonic, carboxylic acids or mixtures thereof.

More precisely, the phosphonic acid may be a phosphonic mono-, di- or tri-acid. The generic term "phosphonic acid" refers to a member of the class of organic acids with the general formula $ROP(OH)_2$ or $RP(=O)(OH)_2$, where R may be chosen from alkyl, halogenated alkyl, aryl, halogenated aryl.

In particular, the sulfonic acid may be a sulfonic mono-, di- or tri-acid. The generic term "sulfonic acid" refers to a member of the class of organic acids with the general formula $R—S(=O)_2—OH$, where R may be chosen from alkyl, halogenated alkyl, aryl, halogenated aryl.

In particular, the carboxylic acid may be a carboxylic mono-, di- or tri-acid. The generic term "carboxylic acid" refers to a member of the class of organic acids with the general formula $R—C(=O)—OH$, where R may be chosen from alkyl, halogenated alkyl, aryl, halogenated aryl. In some particular embodiment, R may also be a polymer and in particular a polymer comprising perfluoroalkane recurring units. Such products are for example commercialized under the trade name Flemion Ion® sold by Asahi Glass.

In a more preferred embodiment, the "at least one acid" used in the process according to the present invention is a sulfonic or a carboxylic acid. Still more preferably, the acid is a halogenated alkane carboxylic acid or a halogenated alkane sulfonic acid. Even more preferably, the acid is a fluorinated alkane carboxylic acid or a fluorinated alkane sulfonic acid. Most preferably, the acid is a perfluorinated alkane carboxylic acid or a perfluorinated alkane sulfonic acid. Excellent results were obtained when the acid was trifluoroacetic acid (TFA) or trifluoromethanesulfonic acid (TfOH) or nonafluorobutane-1-sulfonic acid.

In a particular embodiment, the "at least one acid" used in the process according to the present invention is preferably boric acid or a mixture of a perfluorinated alkane carboxylic acid or a perfluorinated alkane sulfonic acid with boric acid. More preferably, the "at least one acid" is a mixture of trifluoroacetic acid and boric acid.

In another preferred embodiment, the "at least one acid" used in the process according to the present invention is preferably a sulfonic or a phosphonic acid. More preferably, the acid is an aryl sulfonic acid or an aryl phosphonic acid.

The sulfur trioxide used in the process according to the present invention may be gaseous or liquid. It is preferably gaseous. Oleum or fuming sulfuric acid may also be used.

The term "halobenzene" is intended to denote any halogenated derivative of benzene. It may be mono-, di- or tri-halogenated. The halobenzene is preferably a monohalobenzene where the halogen atom is chosen from chloride, fluoride, bromide and iodide. More preferably, the halobenzene is monochlorobenzene (MCB).

The process of the invention for the preparation of 4,4'-dichlorodiphenyl sulfone, starting from MCB and TFA can be described according to the following reaction scheme (Scheme I):

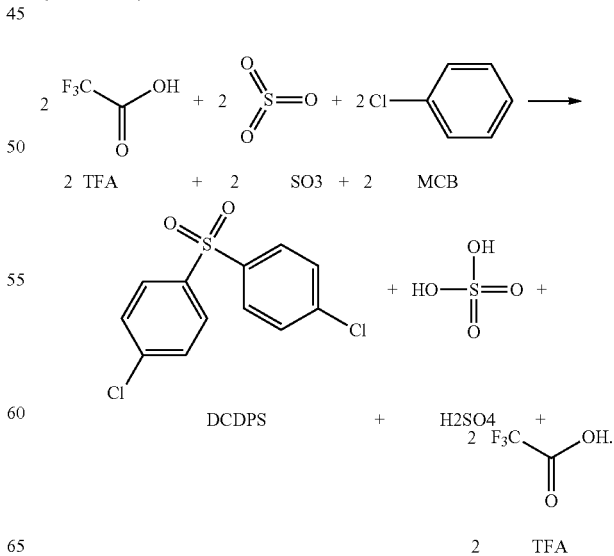

Similarly, the process for the preparation of 4,4'-bis-(4-chlorophenylsulfonyl)biphenyl, can be described according to the following Scheme (II):

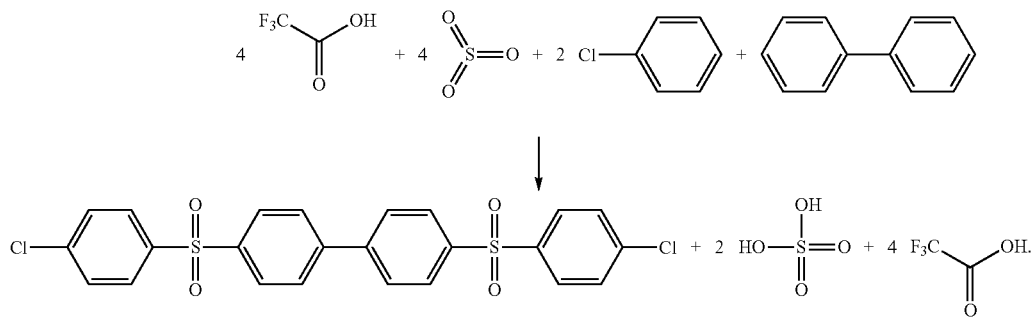

The process may be carried out in one single step, in one pot, as shown in Scheme I and II, or in several steps. For example the preparation of 4,4'-bis-(4-chlorophenylsulfonyl) biphenyl may proceed first with the formation of 4-chlorobenzene sulfonic acid followed by reaction of the same with biphenyl in the presence of at least one acid and sulfur trioxide as follows (Scheme III):

Step 1:

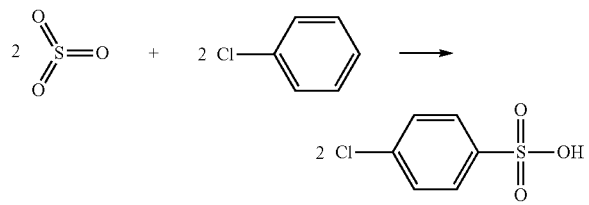

Step 2:

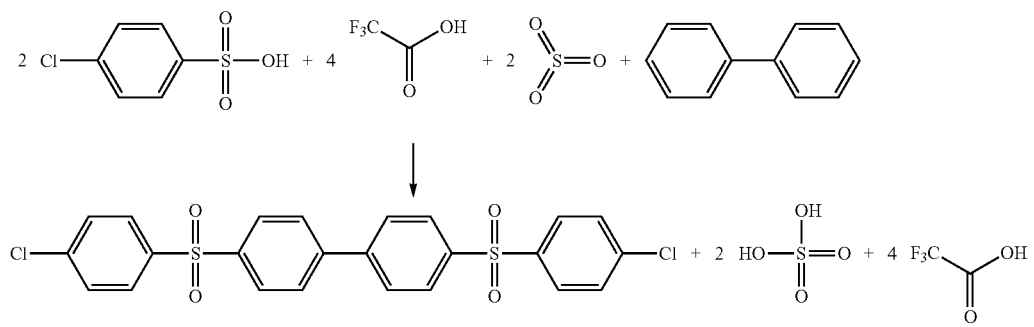

The process according to the present invention is preferably carried out at each step of the process at a temperature of below 200° C., more preferably of below 180° C., still more preferably of below 160° C. and most preferably of below 140° C. On the other hand, the process according to the present invention is preferably carried out at a temperature of above −40° C., more preferably of above 0° C., still more preferably of above 20° C. and most preferably of above 40° C.

The process according to the present invention is preferably carried out at a pressure of below 10 atm, more preferably of below 7 atm, still more preferably of below 5 atm and most preferably of below 2 atm. On the other hand, the process according to the present invention is preferably carried out at a temperature of above 0.5 atm, more preferably of above 0.6 atm, still more preferably of above 0.7 atm and most preferably of above 0.8 atm. Excellent results were obtained when the process according to the present invention was carried out at atmospheric pressure.

The process according to the present invention is preferably carried out under inert atmosphere, typically a nitrogen atmosphere, and essentially under anhydrous conditions.

In a particular embodiment, the process according to the present invention comprises the following steps (a) to (e):
(a) The at least one acid and the at least one halobenzene are added to a reaction medium at a temperature T1;
(b) The reaction medium is maintained at a temperature T2;
(c) Sulfur trioxide is added to the reaction medium;
(d) The reaction medium is maintained at a temperature T3;
(e) The molecule (M) is isolated from the reaction medium.

In step (a), the temperature T1 is preferably of below 100° C., more preferably of below 80° C., still more preferably of below 60° C. and most preferably of below 40° C. On the other hand, the temperature T1 is preferably of above −40° C., more preferably of above −20° C., still more preferably of above 0° C. and most preferably of above 10° C. Excellent results were obtained when T1 was room temperature.

After step (a), the reaction medium is preferably maintained at a temperature T2. The temperature T2 is preferably of below 120° C., more preferably of below 100° C., still more preferably of below 90° C. and most preferably of below 80° C. On the other hand, the temperature T2 is preferably of above −20° C., more preferably of above 0° C., still more preferably of above 10° C. and most preferably of above 20° C. Excellent results were obtained when T2 was comprised between 30 and 70° C.

In step (c), the sulfur trioxide is preferably added very slowly. Typically, the sulfur trioxide is added over a time of from 5 minutes to 10 hours, depending on the cooling capacity of the reaction medium. The reaction medium is preferably maintained at temperature T2 by external cooling means.

During step (d), the temperature is preferably maintained at a temperature T3. The temperature T3 is preferably of below 140° C., more preferably of below 130° C., still more preferably of below 120° C. and most preferably of below 110° C. On the other hand, the temperature T3 is preferably of above 0° C., more preferably of above 10° C., still more preferably of above 20° C. and most preferably of above 30° C. Good results were obtained when T3 was comprised between 30 and 110° C. Excellent results were also obtained when the process was carried out by adding a step (d*) where the reaction medium was maintained at a temperature T3', different from temperatures T3. The temperature T3' is chosen according to the preferred ranges described for the temperature T3 detailed above.

The reaction medium is preferably homogeneous.

In another particular embodiment, the process according to the present invention comprises the following steps (a') to (k'):
(a') The at least one halobenzene is added to a first reaction medium at a temperature T1*
(b') The first reaction medium is maintained at a temperature T2*;
(c') Sulfur trioxide is added to the first reaction medium to form an anhydrous halobenzene sulfonic acid;
(d') The at least one acid is added to a separate second reaction medium at a temperature T3*;
(e') Sulfur trioxide is added to the second reaction medium;
(f') The second reaction medium is maintained at a temperature T4*;
(g') The first reaction medium is then combined with the second reaction medium to obtain a third reaction medium at a temperature T5*;
(h') The third reaction medium is maintained at a temperature T6*;
(i') Optionally, an additional amount of the at least one halobenzene or an aromatic compound (A) is added to the third reaction medium at a temperature T7*;
(j') The third reaction medium is maintained at a temperature T8*;
(k') The molecule (M) is isolated from the third reaction medium.

In steps (a') and (b'), the temperatures T1* and T2* are chosen according to the preferred ranges described for the temperatures T1 and T2 detailed above.

In step (c'), the sulfur trioxide is preferably added very slowly. Typically, the sulfur trioxide is added over a time of from 5 minutes to 10 hours, depending on the cooling capacity of the reaction medium. The reaction medium is preferably maintained at temperature T2* by external cooling means.

In step (d'), the temperature T3* is preferably of below 100° C., more preferably of below 80° C., still more preferably of below 60° C. and most preferably of below 50° C. On the other hand, the temperature T3* is preferably of above −40° C., more preferably of above −20° C., still more preferably of above 0° C. and most preferably of above 20° C. Excellent results were obtained when T3* was 45° C.

In step (f'), the second reaction medium is preferably maintained at a temperature T4*. The temperature T4* is preferably of below 120° C., more preferably of below 110° C., still more preferably of below 100° C. and most preferably of below 90° C. On the other hand, the temperature T4* is preferably of above −20° C., more preferably of above 0° C., still more preferably of above 10° C. and most preferably of above 20° C. Excellent results were obtained when T4* was comprised between 30 and 80° C.

Excellent results were also obtained when the process was carried out by adding a step (f'*) where the reaction medium was maintained at a temperature T4'*, different from temperature T4*. The temperature T4'* is chosen according to the preferred ranges described for the temperature T4* detailed above.

In step (g'), the temperature T5* is preferably of below 120° C., more preferably of below 100° C., still more preferably of below 80° C. and most preferably of below 60° C. On the other hand, the temperature T5* is preferably of above −40° C., more preferably of above −20° C., still more preferably of above 0° C. and most preferably of above 10° C. Excellent results were obtained when T5* comprised between 20 and 50° C.

In step (h'), the reaction medium is preferably maintained at a temperature T6*. The temperature T6* is chosen according to the preferred ranges described for the temperature T4* detailed above.

In step (i'), the temperature T7* is preferably of below 140° C., more preferably of below 120° C. On the other hand, the temperature T7* is preferably of above −40° C., more preferably of above −20° C., still more preferably of above 0° C. and most preferably of above 10° C. Excellent results were obtained when T7* was comprised between 30 and 100° C.

In step (i'), one may optionally add an additional amount of the at least one halobenzene or an aromatic compound (A) to the third reaction medium, depending on the structure of the molecule (M) to be synthesized. The aromatic compound (A) is intended to denote any molecule comprising at least one aromatic group. Preferably, the aromatic compound (A) comprises at least two aromatic groups. Non-limiting examples of such aromatic compound (A) are: benzene, biphenyl, (ortho, meta or para) terphenyl, fluorene, naphthalene, anthracene, etc. For the synthesis of 4,4'-bis-(4-chlorophenylsulfonyl) biphenyl, biphenyl is used as the aromatic compound (A). The aromatic compound (A) is in fact the precursor of the $Ar^3$ structure in the molecule (M).

After step (i'), the third reaction medium is preferably maintained at a temperature T8*. The temperature T8 is chosen according to the preferred ranges described for the temperature T2 detailed above.

The reaction medium is preferably homogeneous but in some cases, the final product (M) can precipitate out of the solution during the synthesis and/or the aromatic compound (A) can be insoluble in the reaction medium.

The multistep process described above is particularly well adapted for the synthesis of asymmetric sulfones of the general formula $Ar^1$—$SO_2$—$Ar^2$ wherein $Ar^1$ and $Ar^2$ are both aromatic groups but are different. In that case, $Ar^1X$, a halobenzene where X is as described above, is added in step (a'), while $Ar^2X$, is added at step (i').

The molecule (M) may be isolated from the reaction medium by precipitation, crystallization or extraction. Good results were obtained when the molecule (M) and in particular 4,4'-dichlorodiphenyl sulfone was isolated by precipitation in water or in methanol, by liquid-liquid extraction or by distillation under vacuum.

At the end of the reaction, the at least one acid can be recycled. Recycling may be achieved by simple physical separation. Since the acid(s) used according to the present invention is (are) true catalyst(s), i.e. they are found intact in the reaction medium after the reaction, it (they) can be used in substoichiometric amounts, which is economically attractive.

The process according to the present invention is preferably carried out using specific molar ratios of the different reagents.

Preferably, the molar ratio of the sulfur trioxide to the at least one halobenzene is from 0.17 to 1.2, more preferably from 0.25 to 1. Excellent results were obtained when the ratio was of about 0.42.

Preferably, the molar ratio of the at least one acid to the at least one halobenzene is from 0.1 to 10, more preferably from 0.5 to 5, most preferably from 2 to 4. Excellent results were obtained when the ratio was of about 3.

The process according to the present invention is preferably carried out in the absence of any other liquid than the reagents, which is economically more profitable. However, solvents may also be used to dilute the reaction medium such as nitromethane, nitrobenzene, dichloromethane, 1,2-dichloroethane, chloroform, 1,1,2,2-tetrachloroethane, 1,2-dichlorobenzene, 1,2,4-trichlorobenzene, carbon disulfide, trichloroethylene, alkanes, petroleum ether and N-methylpyrrolidone.

The process according to the present invention is preferably carried out in one pot. The term "one pot" when referred to a reaction is generally intended to denote any reaction where a reactant is subjected to successive chemical reactions in just one reactor, thereby avoiding a lengthy separation process and purification of the intermediate chemical compounds.

In a particular embodiment, the process according to the present invention is preferably carried out in the presence of a further catalyst, in addition to the at least one acid. If present, the catalyst is preferably used in an amount of 0.2 to 50 g per mol. of halobenzene, more preferably from 1 to 10 g and most preferably from 2 to 5 g. The catalyst optionally used in the present invention may be heterogeneous or homogeneous.

Non limitative examples of homogeneous catalysts are $ZnCl_2$ and $AlCl_3$.

Homogeneous catalysts may also be deposited on solid support such as clay, alumina, silica and zeolites.

The process according to the present invention is preferably carried out in the presence of an acid catalyst.

In some particular embodiment, the catalyst is heterogeneous. Preferably, it is a solid acid catalyst. More preferably, the catalyst is selected from the group consisting of aluminosilicates, perfluoroalkanesulfonic acid resin and mixed oxide.

The solid acid catalyst is selected from the group of aluminosilicates, perfluoroalkanesulfonic acid resin (such as Nafion®-type) or mixed oxide (such as sulfated zirconia). Suitable aluminosilicates are crystalline aluminosilicates like acid-treated clays, for instance montmorillonite K10 and analogs, and zeolites, e.g. H-beta with $SiO_2/Al_2O_3$ ratio≤40. The H-beta zeolite is the preferred catalyst. The catalyst shape is related to the process envisioned: pellets for fixed bed or powder for a slurry-type reactor. Both forms of catalyst are commercially available.

Depending on the quantity and the reactivity of the reagents, the conditions chosen for carrying out the process according to the invention, the reaction can take place in a few minutes or in several hours.

Still another aspect of the present invention is directed to the use of mineral, sulfonic, carboxylic acids or mixtures thereof in the presence of sulfur trioxide for the synthesis of a molecule (M), preferably a dihalodiphenylsulfone.

Should the disclosure of any patents, patent applications, and publications which are incorporated herein by reference conflict with the description of the present application to the extent that it may render a term unclear, the present description shall take precedence.

EXAMPLES

Examples 1 to 9 below relate to the synthesis of 4,4'-dichlorodiphenyl sulfone. Examples 1 to 5 were carried out according to the present invention and feature surprisingly a very high level of regioselectivity and moderate to good yields when reagents and conditions are tuned (see table 1).

Examples 10 and 11 relate to the synthesis of 4,4'-bis-(4-chlorophenylsulfonyl)biphenyl and 4,4''-bis-(4-chlorophenylsulfonyl)terphenyl and were carried out according to the present invention.

The following reagents were used to carry out the examples:
Halobenzene: Monochlorobenzene (MCB, PPG, 99%).
Acids: Trifluoromethanesulfonic acid (TfOH, Aldrich, 98%) or trifluoroacetic acid (TFA, Aldrich, 99%)
Solid acid catalysts: zeolite H-beta from Zeochem: Zeocat® PB-H 25 powder, $SiO_2/Al_2O_3$=30.3 mol/mol, 524 m$^2$/g BET surface area, 8-10 µm average particle size or Zeocat® PB-H 25, pellets, 2.0-3.0 mm, both dried at 500° C. under air for 12 hours before use.
Aromatic compound: Biphenyl (Aldrich, 99.5%)

Example 1

With TfOH, in the Absence of a Solid Acid Catalyst

In a dry 3-neck 250-mL round bottom flask, containing a PTFE-coated stir bar and fitted with a PTFE-coated thermocouple, a distillation receiver allowing returning the vapors to the mixture (Barrett trap)+reflux condenser+$H_2SO_4$ scrubber, and a inlet tube connected to an oleum distillation set up and a nitrogen inlet, were introduced successively, under nitrogen:
1. 100.00 g TfOH
2. 56.29 g MCB.

The flask was then sealed and the mixture was heated to 40° C. under agitation. When the mixture had reached 40° C., 34.00 g of $SO_3$ vapors were slowly introduced to the reactor from an adjacent oleum distillation set up. The addition lasted 60 minutes, during which the temperature was maintained at 40° C. by applying external cooling to the reaction flask. At the end of the addition, the reaction medium was held at 40° C. for 1 hour, then heated to 55° C. The reaction medium was held at 55° C. for 1 hour. The reaction medium temperature was increased to 70° C. and the reaction medium was held at 70° C. for 1 hour. The reaction medium temperature was increased to 100° C. and the reaction medium was held at 100° C. for 1 hour. At the end of the reaction, the reaction medium was poured on 2,000 mL of deionized water. The precipitate formed was isolated by filtration, rinsed with more deionized water (2,000 mL) and dried at 60° C. under 0.13 atm for 20 hours. The dried solid (51.06 g) was analyzed by GC and shown to be 4.4'-dichlorodiphenyl sulfone (96.7% of the 4,4'-isomer), 84% yield.

Example 2

With TFA, in the Presence of a Solid Acid Catalyst

In a dry 3-neck 250-mL round bottom flask, containing a PTFE-coated stir bar and fitted with a PTFE-coated thermocouple, a distillation receiver allowing returning the vapors to the mixture (Barrett trap)+reflux condenser+$H_2SO_4$ scrubber, and a inlet tube connected to an oleum distillation set up and a nitrogen inlet, were introduced successively, under nitrogen:
1. 71.40 g TFA
2. 5.69 g zeolite H-beta powder
3. 87.80 g MCB.

The flask was then sealed and the mixture was heated to 60° C. under agitation. When the mixture had reached 60° C., 50.00 g of $SO_3$ vapors were slowly introduced to the reactor from an adjacent oleum distillation set up. The addition lasted 60 minutes, during which the temperature was maintained at 60° C. by applying external cooling to the reaction flask. At the end of the addition, the reaction medium was cooled down to 40° C. and held at 40° C. for 1 hour, then heated to 55° C. The reaction medium was held at 55° C. for 1 hour. The reaction medium temperature was increased to 70° C. and the reaction medium was held at 70° C. for 1 hour. The reaction medium temperature was increased to 100° C. and the reaction medium was held at 100° C. for 1 hour. At the end of the reaction, the catalyst was removed by filtration under pressure (0.7 μm glass fiber filter GF/F) and the filtrate was poured on 2,000 mL of deionized water. The precipitate formed was isolated by filtration, rinsed with more deionized water (2,000 mL) and dried at 60° C. under 0.13 atm for 20 hours. The dried solid (26.47 g) was analyzed by GC and shown to be 4.4'-dichlorodiphenyl sulfone (96.7% of the 4,4'-isomer), 30% yield.

Example 3

With TFA, in the Absence of a Solid Acid Catalyst

In a dry 3-neck 250-mL round bottom flask, containing a PTFE-coated stir bar and fitted with a PTFE-coated thermocouple, a distillation receiver allowing returning the vapors to the mixture (Barrett trap)+reflux condenser+$H_2SO_4$ scrubber, and a inlet tube connected to an oleum distillation set up and a nitrogen inlet, were introduced successively, under nitrogen:
1. 71.86 g TFA
2. 88.02 g MCB.

The flask was then sealed and the mixture was heated to 70° C. under agitation. When the mixture had reached 70° C., 65.00 g of $SO_3$ vapors were slowly introduced to the reactor from an adjacent oleum distillation set up. The addition lasted 60 minutes, during which the temperature was maintained at 70° C. by applying external cooling to the reaction flask. At the end of the addition, the reaction medium was held at 70° C. for 24 hours. At the end of the reaction, the reaction medium was poured on 2,000 mL of deionized water. The precipitate formed was isolated by filtration, rinsed with more deionized water (2,000 mL) and dried at 60° C. under 0.13 atm for 20 hours. The dried solid (20.36 g) was analyzed by GC and shown to be 4.4'-dichlorodiphenyl sulfone (95.8% 4,4'-isomer), 17% yield.

Example 4

Multistep Process with TFA, in the Absence of a Solid Acid Catalyst

In a dry 250 mL jacketed addition funnel, with pressure equalizing, maintained under a nitrogen blanket, fitted with an inlet tube connected to an oleum distillation set up, were introduced 213.67 g of TFA. The jacket of the addition funnel was heated to 45° C. and 75.02 g of $SO_3$ vapors were slowly introduced into the TFA via a glass frit. The total time of addition was 2 hours. The mixture of trifluoroacetosulfate was then held at 45° C. for 3 hours and cooled down to 5° C. for storage. A blanket of nitrogen was maintained on the mixture at all time.

In a dry 3-neck 250-mL round bottom flask, containing a PTFE-coated stir bar and fitted with a PTFE-coated thermocouple, a distillation receiver allowing returning the vapors to the mixture (Barrett trap)+reflux condenser+$H_2SO_4$ scrubber, and connected to the jacketed addition funnel containing the trifluoroacetosulfate, was introduced, under nitrogen, a third of the trifluoroacetate mixture prepared as described above (25.00 g $SO_3$+71.22 g TFA). 43.15 g of molten 4-chlorobenzene sulfonic acid (93 wt % pure) as prepared in comparative example 6 were added to the Barrett trap, along with 47.52 g of TFA. The trifluoroacetosulfate mixture was heated to 40° C. in the reaction flask. The mixture of 4-chlorobenzenesulfonic acid and TFA in the Barrett trap was then added slowly over 30 minutes to the reaction flask, under agitation. 24.61 g of MCB were then added to the Barrett trap and added slowly over 30 minutes to the reaction flask. The reaction medium was heated to 60° C. under agitation. The reaction medium was held at 60° C. for 3 hours. The temperature was increased to 100° C. with the Barrett trap in the collection position. 85.06 g of distillate were collected in the Barrett trap and removed. The Barrett trap was put in total reflux position again and the reaction medium was held at 100° C. for 5 hours.

At the end of the reaction, the mixture was poured on 2,000 mL of deionized water. The precipitate formed was isolated by filtration, rinsed with more deionized water (2,000 mL) and dried at 60° C. under 0.13 atm for 20 hours. The dried solid (9.480 g) was analyzed by GC and shown to be 4.4'-dichlorodiphenyl sulfone (98.9% 4,4'-isomer), 11% yield. Taking into account the isomer purity of the dichlorodiphenyl sulfone present in the starting 4-chlorobenzenesulfonic acid (97.3%), the regioselectivity of the reaction with the trifluoroacetosulfate is 99.6%.

Example 5

Multistep Process with TFA, in the Presence of a Solid Acid Catalyst

The procedure of example 4 was repeated except that 5.2064 g of zeolite H-beta pellets were added to the trifluoroacetate in the reaction flask, before the start of addition of 4-chlorobenzene sulfonic acid. At the end of the reaction, the catalyst was removed by filtration on Buchner funnel and the filtrate was poured on 2,000 mL of deionized water. The precipitate formed was isolated by filtration, rinsed with more deionized water (2,000 mL) and dried at 60° C. under 0.13 atm for 20 hours. The dried solid (11.760 g) was analyzed by GC and shown to be 4.4'-dichlorodiphenyl sulfone (97.1% 4,4'-isomer), 14% yield. Taking into account the isomer purity of the dichlorodiphenyl sulfone present in the starting 4-chlorobenzenesulfonic acid (97.3%), the regioselectivity of the reaction with the trifluoroacetosulfate is 97.0%.

Comparative Example 6

In the Absence of TFA or TfOH

In a dry 3-neck 250-mL round bottom flask, containing a PTFE-coated stir bar and fitted with a PTFE-coated thermocouple, a distillation receiver allowing returning the vapors to the mixture (Barrett trap)+reflux condenser+$H_2SO_4$ scrubber, and a inlet tube connected to an oleum distillation set up and a nitrogen inlet, was introduced, under nitrogen 225.12 g of MCB.

The flask was then sealed and the mixture was cooled down to 10° C. When the mixture had reached 10° C., 21.50 g of $SO_3$ vapors were slowly introduced to the reactor from an adjacent oleum distillation set up. The addition lasted 60 minutes, during which the temperature was maintained at 10° C. by applying external cooling to the reaction flask. At the end of the reaction, the mixture was poured on 2,000 mL of deionized water. The precipitate formed was isolated by filtration, rinsed with more deionized water (2,000 mL) and dried at 60° C. under 0.13 atm for 20 hours. The dried solid (3.527 g) was analyzed by GC and shown to be 4,4'-dichlorodiphenyl sulfone (97.3% 4,4'-isomer), 4% yield.

The product of comparative example 6 was in fact mainly composed of 4-chlorobenzene sulfonic acid. 52.30 g of 4-chlorobenzenesulfonic acid (93 wt % pure, 0.252 mol) was isolated by evaporation of the excess monochlorobenzene from the final reaction medium under reduced pressure. The resulting solid contains also 4,4'-dichlorodiphenyl sulfone (6.7 wt %) and sulfuric acid (0.3 wt %).

Comparative Examples 7, 8 and 9

U.S. Pat. No. 4,983,773 describes the synthesis of 4,4'-dichlorodiphenyl sulfone in its examples 1, 2 and 3. Boric acid and trifluoromethanesulfonic acid (TfOH) are respectively used in examples 2 and 3 as catalysts. In the absence of added acid (i.e. phosphonic, sulfonic, carboxylic acids such as TFA or TfOH), temperatures of 200-250° C. are required to obtain similar yields but this is achieved at the expense of the reaction selectivity.

The solid was introduced a dry 3-neck 250-mL round bottom flask, containing a PTFE-coated stir bar and fitted with a PTFE-coated thermocouple, a distillation receiver allowing returning the vapors to the mixture (Barrett trap)+reflux condenser+$H_2SO_4$ scrubber, and a inlet tube connected to an oleum distillation set up and a nitrogen inlet. Under nitrogen 57.47 g trifluoroacetic acid (0.504 mol) was then introduced into the flask. The flask was then sealed and the mixture was heated to 40° C. under agitation. When the mixture reached 40° C., 20.17 g of $SO_3$ vapors (0.252 mol) were slowly introduced to the reactor from an adjacent oleum distillation set up. The addition lasts 60 minutes, during which the temperature was maintained at 40° C. by applying external cooling to the reaction flask. At the end of the addition, 19.43 g biphenyl (0.126 mol) were added to the flask and the temperature of the reaction medium was increased to 100° C. and held at 100° C. for 5 hours. A solid forms rapidly in the reaction medium. At the end of the reaction, the mixture was poured on 2,000 mL of isopropanol. The solid was isolated by filtration, rinsed with more isopropanol (2,000 mL) and dried at 60° C. under 0.13 atm for 20 hours. The dried solid (9.51 g, 15% yield) was analyzed by HPLC and shown to be 4,4'-bis-(4-chlorophenylsulfonyl)biphenyl by comparison with a commercially available sample (Aldrich, 98%).

Example 11

Preparation of 4,4''-bis-(4-chlorophenylsulfonyl)terphenyl with TFA, in the absence of a solid acid catalyst The same procedure as for example 10 was followed except that instead of biphenyl, 29.02 g of p-terphenyl (Aldrich, 99+%) was used, producing 7.3 g of 4,4''-bis-(4-chlorophenylsulfonyl)terphenyl (10% yield), whose structure was confirmed by $^1$H NMR (DMSO-$d_6$).

TABLE 1

Synthesis of 4,4'-dichlorodiphenyl sulfone - Experimental results

| Example | Reagents | Maximum temperature | Catalyst | DCDPS yield (mol %) | 4,4'-DCDPS selectivity (mol %) |
|---|---|---|---|---|---|
| 1 | TfOH—$SO_3$-MCB | 100° C. | None | 84 | 96.7 |
| 2 | TFA-$SO_3$-MCB | 100° C. | Solid acid H-β zeolite/Zeochem | 30 | 96.7 |
| 3 | TFA-$SO_3$-MCB | 70° C. | None | 17 | 95.8 |
| 4 | TFA-$SO_3$-MCB | 100° C. | None | 11 | 99.6 |
| 5 | TFA-$SO_3$-MCB | 100° C. | Solid acid H-β zeolite/Zeochem | 14 | 97.0 |
| C6 | $SO_3$-MCB | 10° C. | None | 4 | 97.3 |
| C7 | $H_2SO_4$-MCB | 240° C. | None | 68 | 79 |
| C8 | $H_2SO_4$-MCB | 240° C. | Boric acid | 84 | 84.8 |
| C9 | $H_2SO_4$-MCB | 240° C. | TfOH | 75 | 89.3 |

Example 10

Preparation of 4,4'-bis-(4-chlorophenylsulfonyl)biphenyl with TFA, in the absence of a solid acid catalyst The product of example 6 was mainly composed of 4-chlorobenzene sulfonic acid. 52.30 g of 4-chlorobenzenesulfonic acid (93 wt % pure, 0.252 mol) was isolated by evaporation of the excess monochlorobenzene from the final reaction medium under reduced pressure. The resulting solid contained also 4,4-dichlorodiphenyl sulfone (6.7 wt %) and sulfuric acid (0.3 wt %).

The invention claimed is:

1. A process for making a molecule of the formula (M):

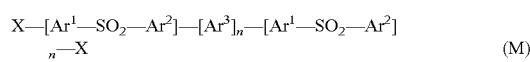

(M)

wherein:

n and m are independently 0, 1, 2, 3 or 4;

X is a halogen selected from chlorine, fluorine, bromine and iodine;

$Ar^1$, $Ar^2$ are equal or different from each other and are aromatic moieties of the formula:

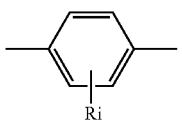

Ar³ is selected from the group consisting of:

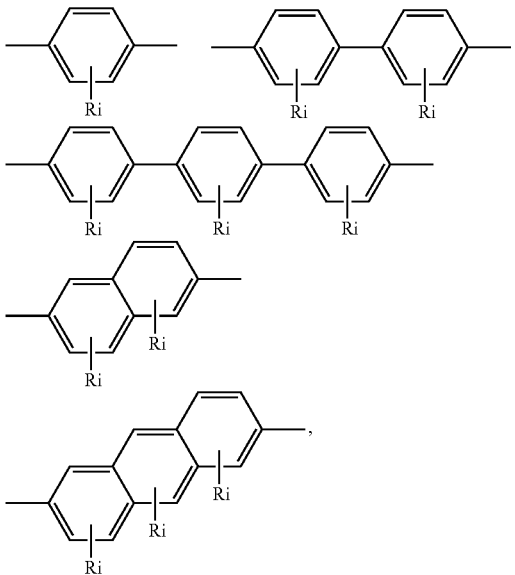

and
each Ri is independently selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
by reacting together at least one fluorinated acid, sulfur trioxide, at least one halobenzene, and optionally, an aromatic compound, wherein the at least one fluorinated acid is selected from the group consisting of fluorinated alkane sulfonic acid, fluorinated alkane carboxylic acid, and mixtures thereof.

2. The process according to claim 1, wherein the molecule of formula (M) comprises 4,4'-dichlorodiphenyl sulfone or 4,4'-bis-(4-chlorophenylsulfonyl)biphenyl.

3. The process according to claim 1, wherein the fluorinated alkane carboxylic acid is trifluoroacetic acid.

4. The process according to claim 1, wherein the fluorinated alkane sulfonic acid is trifluoromethanesulfonic acid.

5. The process according to claim 1, wherein the process comprises the following steps:
(a) the at least one fluorinated acid and the at least one halobenzene are added to a reaction medium at a temperature T1;
(b) the reaction medium is maintained at a temperature T2;
(c) sulfur trioxide is added to the reaction medium;
(d) the reaction medium is maintained at a temperature T3;
(e) the molecule of formula (M) is isolated from the reaction medium.

6. The process according to claim 1, wherein the process is done in one pot.

7. The process according to claim 1, wherein the process is carried out in the presence of a solid catalyst.

8. The process according to claim 7, wherein the solid catalyst is an acid catalyst.

9. The process according to claim 8, wherein the solid acid catalyst is selected from the group consisting of aluminosilicates, perfluoroalkanesulfonic acid resin, and mixed oxide catalysts.

10. The process according to claim 1, wherein the process comprises the following steps (a') to (k'):
(a') the at least one halobenzene is added to a first reaction medium at a temperature T1*;
(b') the first reaction medium is maintained at a temperature T2*;
(c') sulfur trioxide is added to the first reaction medium to form an anhydrous halobenzene sulfonic acid;
(d') the at least one fluorinated acid is added to a separate second reaction medium at a temperature T3*;
(e') sulfur trioxide is added to the second reaction medium;
(f') the second reaction medium is maintained at a temperature T4*;
(g') the first reaction medium is then combined with the second reaction medium to obtain a third reaction medium at a temperature T5*;
(h') the third reaction medium is maintained at a temperature T6*;
(i') optionally, an additional amount of the at least one halobenzene or an aromatic compound (A) is added to the third reaction medium at a temperature T7*;
(j') the third reaction medium is maintained at a temperature T8*;
(k') the molecule of formula (M) is isolated from the third reaction medium.

11. The process according to claim 10, wherein T5* is of below 120° C.

12. The process according to claim 1, wherein the aromatic compound is selected from benzene, biphenyl, terphenyl, fluorene, naphthalene, and anthracene.

13. The process according to claim 1, wherein the molecule of formula (M) is made by reacting together the at least one fluorinated acid, sulfur trioxide, and the at least one halobenzene, and wherein n=0, and m=0.

14. The process of claim 13, wherein the at least one fluorinated acid is trifluoromethanesulfonic acid or trifluoroacetic acid, the at least one halobenzene is monochlorobenzene, and the molecule of formula (M) is 4,4'-dichlorodiphenyl sulfone.

15. The process of claim 1, wherein the molecule of formula (M) is made by reacting together the at least one fluorinated acid, sulfur trioxide, the at least one halobenzene, and an aromatic compound selected from benzene, biphenyl, terphenyl, fluorene, naphthalene, and anthracene, and wherein n=1 and m=1.

16. The process of claim 15, wherein the at least one fluorinated acid is trifluoroacetic acid, the at least one halobenzene is monochlorobenzene, the aromatic compound is biphenyl, and the molecule of formula (M) is 4,4"-bis-(4-chlorophenylsulfonyl)biphenyl.

17. The process of claim 15, wherein the at least one fluorinated acid is trifluoroacetic acid, the at least one halobenzene is monochlorobenzene, the aromatic compound is terphenyl, and the molecule of formula (M) is 4,4"-bis-(4-chlorophenylsulfonyl)terphenyl.

18. The process according to claim 1, wherein the at least one fluorinated acid is selected from the group consisting of perfluorinated alkane sulfonic acid, perfluorinated alkane carboxylic acid, and mixtures thereof.

19. The process according to claim 1 further comprising reacting together the at least one fluorinated acid, the sulfur trioxide, the at least one halobenzene, and optionally, the aromatic compound, with boric acid, boronic acid, or mixtures thereof.

20. The process according to claim 1, wherein the at least one fluorinated acid is added to the reaction.

21. The process according to claim 20, wherein the at least one fluorinated acid is a catalyst.

22. The process according to claim 1, wherein a molar ratio of the at least one fluorinated acid to the at least one halobenzene is from 0.5 to 5.

23. The process according to claim 22, wherein the molar ratio is from 2 to 4.

* * * * *